United States Patent
Geyer et al.

[19]

[11] Patent Number: 6,050,125

[45] Date of Patent: Apr. 18, 2000

[54] CALIBRATING WAFER AND METHOD FOR THE PRODUCTION OF A CALIBRATING WAFER

[75] Inventors: Stefan Geyer; Michael Horn, both of Dresden; Ralf Göthel, Schullwitz; Kathrin Kurth, Dresden, all of Germany

[73] Assignee: Siemens Aktiengesellschaft, Munich, Germany

[21] Appl. No.: 09/141,080

[22] Filed: Aug. 27, 1998

[30] Foreign Application Priority Data

Aug. 27, 1997 [DE] Germany ............... 197 37 363

[51] Int. Cl.⁷ ........................................ G01J 1/02
[52] U.S. Cl. ............................................. 73/1.01
[58] Field of Search .................. 73/1.01; 427/422; 356/243.6, 243.4

[56] References Cited

U.S. PATENT DOCUMENTS

| | | |
|---|---|---|
| 4,220,962 | 9/1980 | Sommer et al. . |
| 4,386,850 | 6/1983 | Leahy . |
| 4,473,296 | 9/1984 | Shofner et al. . |
| 4,512,659 | 4/1985 | Galbraith et al. . |
| 4,636,073 | 1/1987 | Williams . |
| 4,739,177 | 4/1988 | Borden . |
| 5,078,492 | 1/1992 | Scheer . |
| 5,144,524 | 9/1992 | Tullis et al. . |
| 5,198,869 | 3/1993 | Monteverde et al. . |
| 5,383,018 | 1/1995 | Sadjadi ................... 356/243.4 |
| 5,534,309 | 7/1996 | Liu ......................... 356/243.6 |

FOREIGN PATENT DOCUMENTS

| | | |
|---|---|---|
| 0 787 981 A2 | 8/1997 | European Pat. Off. . |
| 31 10 631 C2 | 7/1989 | Germany . |

OTHER PUBLICATIONS

Patent Abstracts of Japan No. 1–272939 A (Kageyama), dated Oct. 31, 1989.

*Primary Examiner*—Robert Raevis
*Attorney, Agent, or Firm*—Herbert L. Lerner; Laurence A. Greenberg; Werner H. Stemer

[57] ABSTRACT

A calibrating wafer and a method for the production of a calibrating wafer having polymer microspheres. The polymer microspheres are subjected to a heat treatment in a temperature range in which the polymer microspheres start to soften.

6 Claims, 1 Drawing Sheet

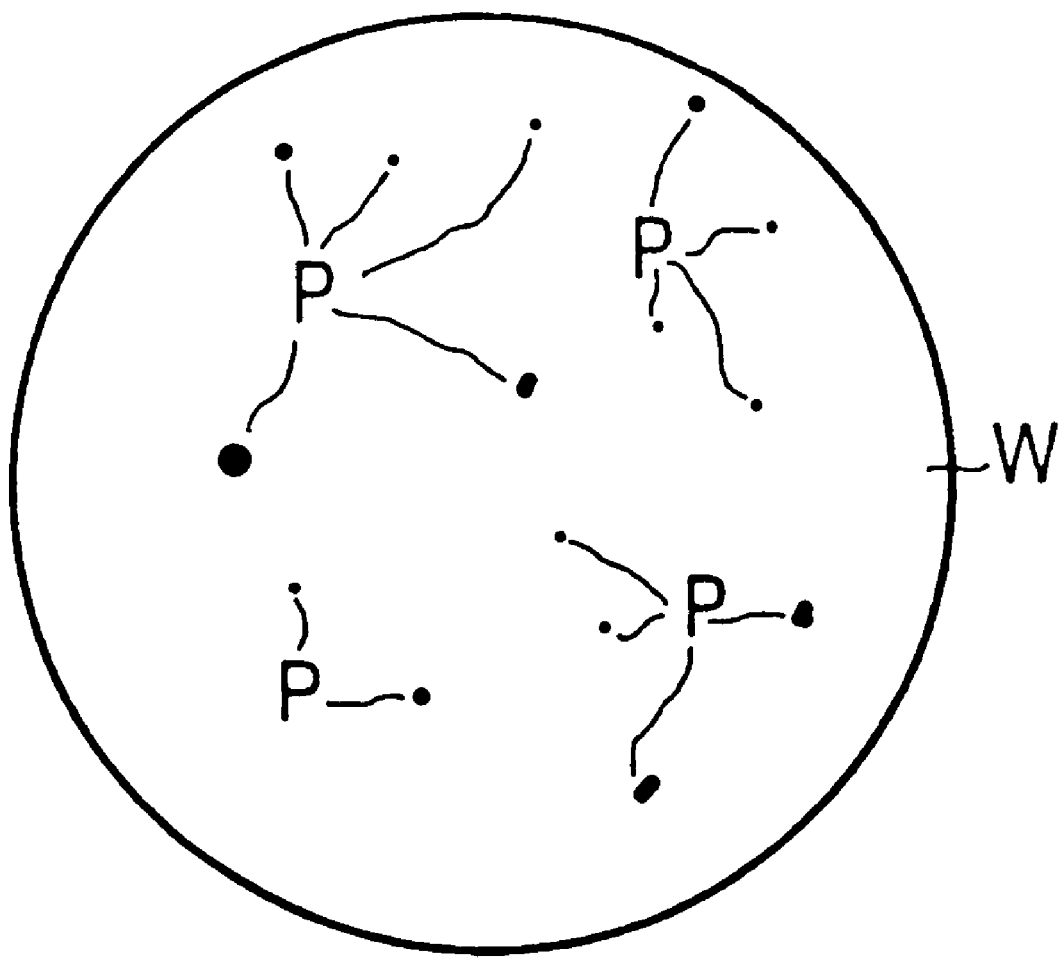

CALIBRATING WAFER AND METHOD FOR THE PRODUCTION OF A CALIBRATING WAFER

BACKGROUND OF THE INVENTION

FIELD OF THE INVENTION

The invention relates to a calibrating wafer having polymer microspheres which adhere thereto. The invention also relates to a method for the production of a calibrating wafer, in which polymer microspheres are applied to the calibrating wafer.

As is known, semiconductor components (for example integrated circuits essentially made of silicon) are produced under so-called clean room conditions, that is to say in an environment containing the least possible amount of so-called particles (dirt). The existence of the respectively required clean room and process conditions is checked regularly as well as when otherwise required (for example due to a reduction in component quality and/or yield), for example by using instruments to measure surface particles. Special wafers, which are generally referred to as calibrating wafers, are used for calibrating the measuring instruments.

Prior art calibrating wafers are semiconductor wafers having a surface which is provided with polymer microspheres, in a specific number and on a specific scale. The polymer microspheres are applied by using a polymer microsphere dispersion diluted to a specific extent. Calibrating wafers which are produced in that way thus have polymer microspheres in a specific amount, in a specific spatial distribution (on the calibrating wafer) and with a specific size distribution. The production method for those calibrating wafers is very expensive. It is true that the calibrating wafers are stored under clean room conditions between the individual checks of the clean room conditions. Nevertheless, since even under the best clean room conditions which can be achieved technically, there are always still traces of, for example, ammonia, hydrochloric acid, hydrofluoric acid or the like in air, they build up over time (including) on the calibrating wafers, for example in the form of ammonium salts. However, over the course of time, those build-ups interfere with the so-called calibration, the effect of which, in the extreme case, is that calibration is no longer possible.

Although as a rule the build-ups can be cleaned off straightforwardly with water, the polymer microspheres are also removed from the wafers at the same time. They therefore need to be re-applied using the heretofore known very expensive method.

SUMMARY OF THE INVENTION

It is accordingly an object of the invention to provide a calibrating wafer and a method for the production of a calibrating wafer, which overcome the hereinafore-mentioned disadvantages of the heretofore-known products and methods of this general type and in which the calibrating wafers, together with polymer microspheres applied to them, can be used more frequently than heretofore.

With the foregoing and other objects in view there is provided, in accordance with the invention, a calibrating wafer, comprising a wafer body; and polymer microspheres adhering to the wafer body; the polymer microspheres fixed by a heat treatment carried out in a temperature range in which the polymer microspheres start to soften.

In accordance with another feature of the invention, the temperature range covers 80° C. to 95° C.

With the objects of the invention in view, there is also provided a method for the production of a calibrating wafer, which comprises applying polymer microspheres to a calibrating wafer by a heat treatment in a temperature range in which the polymer microspheres start to soften.

With the objects of the invention in view, there is additionally provided a method for the production of a calibrating wafer, which comprises applying polymer microspheres to a calibrating wafer; and subsequently subjecting the calibrating wafer together with the applied polymer microspheres to a heat treatment in a temperature range in which the polymer microspheres start to soften.

In accordance with a concomitant mode of the invention, there is provided a method which comprises carrying out the heat treatment at from 80° C. to 95° C.

Other features which are considered as characteristic for the invention are set forth in the appended claims.

Although the invention is illustrated and described herein as embodied in a calibrating wafer and a method for the production of a calibrating wafer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

The FIGURE of the drawing is a diagrammatic, plan view of a calibrating wafer having polymer microspheres.

DESCRIPTION OF THE PREFERRED EMBODIMENTS

Referring now in detail to the single FIGURE of the drawing, there is seen a calibrating wafer W together with polymer microspheres P. In this case the polymer microspheres P represented on the calibrating wafer W are only shown symbolically. As a rule there are substantially more polymer microspheres P on a wafer W of this type than the represented number, and in spite of having different sizes, these polymer microspheres P are always substantially smaller than represented.

In the case of the calibrating wafer W according to the invention, the polymer microspheres P are fixed on the body of the wafer W through the use of a special heat treatment, that is carried out in a temperature range in which the polymer microspheres P just start to soften. In this case a temperature range of from 80° C. to 95° C. has proved favorable as the temperature range. The respective temperature range is naturally dependent on the respective nature of the chosen polymer.

The calibrating wafer W can be produced by carrying out the heat treatment in the chosen temperature range, for example 80° C. to 95° C., either during application of the polymer microspheres P to the calibrating wafer W or not until after the polymer microspheres P have been applied.

The advantage of this type of calibrating wafer W according to the invention, and of the production methods which are disclosed, is that when build-ups (for example the afore-mentioned ammonium salts) are washed off from a calibrating wafer W according to the invention as indicated in the introduction, the polymer microspheres P are not removed as well (as indicated with reference to the prior art). Instead, the polymer microspheres P will remain adhering to the calibrating wafer W because of the heat treatment which has been carried out.

Calibrating wafers W according to the invention can therefore be used substantially more often and for substantially longer periods than those according to the prior art, which leads to a substantial cost saving. The elaborate application of polymer microspheres P is needed substantially less frequently than heretofore. Tests have shown that, in the production and use of calibrating wafers W according to the invention, the number per year can be reduced to 10% of the amount heretofore required.

We claim:

1. A calibrating wafer, comprising:
    a wafer body; and
    a predetermined number of polymer microspheres with a specific size and spatial distribution adhering to said wafer body;
    said polymer microspheres fixed by a heat treatment carried out in a temperature range in which said polymer microspheres start to soften.

2. The calibrating wafer according to claim 1, wherein said temperature range covers 80° C. to 95° C.

3. A method for the production of a calibrating wafer, which comprises:
    applying polymer microspheres to a calibrating wafer by a heat treatment in a temperature range in which the polymer microspheres start to soften.

4. A method for the production of a calibrating wafer, which comprises:
    applying polymer microspheres to a calibrating wafer; and
    subsequently subjecting the calibrating wafer together with the applied polymer microspheres to a heat treatment in a temperature range in which the polymer microspheres start to soften.

5. The method according to claim 3, which comprises carrying out the heat treatment at from 80° C. to 95° C.

6. The method according to claim 4, which comprises carrying out the heat treatment at from 80° C. to 95° C.

* * * * *